United States Patent
Matsumoto

(10) Patent No.: US 8,836,779 B2
(45) Date of Patent: Sep. 16, 2014

(54) INSPECTION DEVICE

(75) Inventor: Saori Matsumoto, Koganei (JP)

(73) Assignee: Olympus Corporation, Tokyo (JP)

( * ) Notice: Subject to any disclaimer, the term of this patent is extended or adjusted under 35 U.S.C. 154(b) by 286 days.

(21) Appl. No.: 13/240,770

(22) Filed: Sep. 22, 2011

(65) Prior Publication Data

US 2012/0081546 A1    Apr. 5, 2012

(30) Foreign Application Priority Data

Sep. 30, 2010   (JP) ................................ 2010-222242

(51) Int. Cl.
*H04N 7/18*   (2006.01)

(52) U.S. Cl.
USPC .............. 348/79; 382/165; 382/191; 382/192

(58) Field of Classification Search
USPC .............................. 348/79; 382/165, 191, 192
See application file for complete search history.

(56) References Cited

U.S. PATENT DOCUMENTS

| | | | |
|---|---|---|---|
| 6,768,102 B1 * | 7/2004 | Skoll .......................... | 250/252.1 |
| 2005/0123181 A1 * | 6/2005 | Freund et al. ................. | 382/128 |
| 2008/0038771 A1 * | 2/2008 | Taylor et al. ................. | 435/40.5 |
| 2008/0240613 A1 * | 10/2008 | Dietz et al. ................... | 382/284 |
| 2008/0292300 A1 * | 11/2008 | van der Veen et al. ........ | 396/311 |

FOREIGN PATENT DOCUMENTS

| | | |
|---|---|---|
| JP | 2006-292999 A | 10/2006 |
| JP | 2008-203237 A | 9/2008 |
| JP | 2009-014354 | 1/2009 |

OTHER PUBLICATIONS

Japanese Office Action dated Jun. 17, 2014 from related Japanese Application No. 2010-222242, together with an English language translation.

* cited by examiner

*Primary Examiner* — Sath V Perungavoor
*Assistant Examiner* — Jeffery Williams
(74) *Attorney, Agent, or Firm* — Scully, Scott, Murphy & Presser, P.C.

(57) ABSTRACT

The present invention provides an inspection device including an imaging unit 16 for imaging an object to be inspected, a characteristics measurement unit 15 for measuring characteristics of the object to be inspected, an inspection information acquisition unit 11 for acquiring inspection information related to the object to be inspected, a condition determination unit 12 for determining measurement information related to a measurement condition of the object to be inspected corresponding to the inspection information, an imaging control unit 14 for controlling imaging by the imaging unit, and a measurement control unit 13 for controlling measurement by the characteristics measurement unit based on the measurement information.

15 Claims, 14 Drawing Sheets

FIG. 8
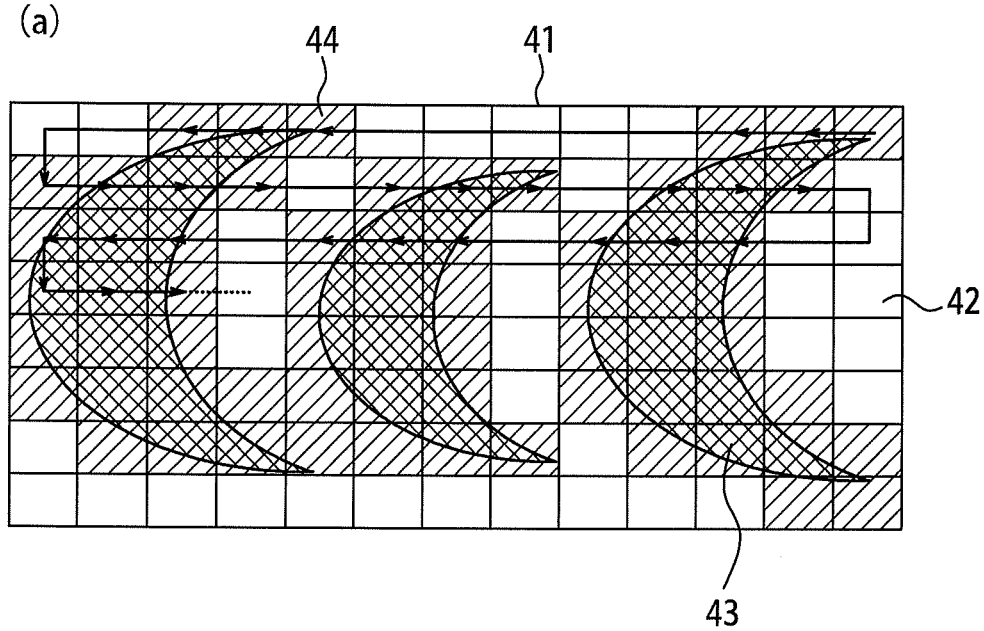
(a)
(b) 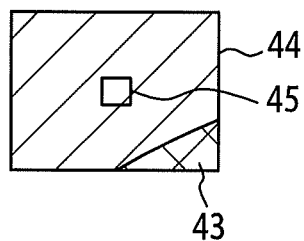
(c) 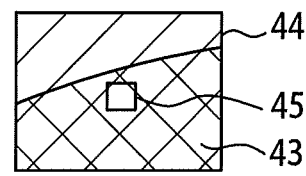
FIG. 9
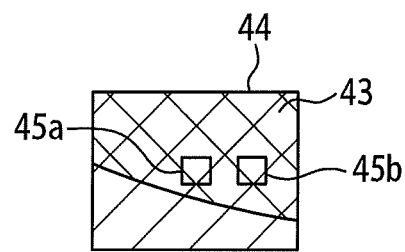

INSPECTION DEVICE

CROSS-REFERENCE TO RELATED APPLICATION

The present application claims priority from Japanese Application No. 2010-222242 filed on Nov. 30, 2010, the content of which is incorporated herein by reference.

BACKGROUND OF THE INVENTION

1. Technical Field

The present invention relates generally to inspection devices such as microscope and inspection apparatus, in particular, to an inspection device for taking an image of an object to be inspected and measuring characteristics of an object to be inspected.

2. Background of the Invention

Recently, sophisticated inspection devices have been developed. The devices are microscope and inspection apparatus capable of taking images of objects to be inspected, such as specimens, of measuring spectroscopic characteristics of the object, and of utilizing their result for an image processing of the object, for diagnosis support, and for an image inspection.

For example, JP2009014354 discloses a device providing stable images of specimens in analyses using microscopes for analyzing stained biological specimens. The device measures spectral characteristics of a plurality of portions in specimens, estimates dying variation in the specimens so as to execute correction of the dying variation.

On the other hand, a device, which divides necessary observation area of the object to be inspected and integrates the divided images acquired by an objective lens of high power with moving the object to be inspected with regard to the objective lens so as to provide a wide field and high resolution digital images effectively.

SUMMARY OF THE INVENTION

To solve problems above, the inspection device of the present invention includes an imaging unit for imaging an object to be inspected, a characteristics measurement unit for measuring characteristics of the object to be inspected, an inspection information acquisition unit for acquiring inspection information related to the object to be inspected, a condition determination unit for determining measurement information related to a measurement condition of the object to be inspected corresponding to the inspection information, an imaging control unit for controlling imaging by the imaging unit, and a measurement control unit for controlling measurement by the characteristics measurement unit based on the measurement information.

In the inspection device of the present invention, the condition determination unit determines the imaging information related to the imaging condition of the object to be inspected corresponding to the inspection information, and the imaging control unit controls imaging by the imaging unit based on the imaging information.

In the inspection device of the present invention, the characteristics measurement unit measures a plurality of spots for characteristics of the object to be inspected.

The inspection device of the present invention further includes an object moving unit for moving the object to be inspected, wherein the imaging control unit divides an imaging area into a plurality of divided imaging areas, controls the imaging unit to image each of the plurality of divided imaging areas, and controls the object moving unit to move the object to be inspected to a next divided imaging area at each time of imaging of one of the plurality of divided imaging areas, and the measurement control unit controls the characteristics measurement unit to selectively execute measurements synchronically with the imaging executed by the imaging control unit.

In the inspection device of the present invention, the measurement information includes information of a number of measurement spots, and the measurement control unit controls the characteristics measurement unit to execute additional measurements until sufficient amount of measurement data comparable to that of the number of measurement spots, after the imaging by the imaging control unit is completed, in the case where an amount of measurement data is insufficient and not comparable to that of the number of measurement spots.

The inspection device of the present invention, further comprises a thumbnail acquisition unit for acquiring thumbnail by imaging the object to be imaged, wherein the imaging control unit acquires location information of measurement regions within the object to be inspected based on the thumbnail, controls the imaging unit to image only measurement unit existing areas, where measurement regions locate, among the divided imaging areas, controls the object moving unit to move the object to be inspected so as to allow the imaging unit to image a next measurement region existing area, at each time of imaging of the measurement region existing area by imaging unit.

The inspection device of the present invention includes the thumbnail acquisition unit for acquiring thumbnail by imaging the object to be inspected and generating the inspection information from the acquired thumbnail, instead of the inspection information acquisition unit.

In the inspection device of the present invention, the inspection information generated by the thumbnail acquisition unit includes color information of the thumbnail.

In the inspection device of the present invention, the measurement information includes information representing determining the randomly selected spots among imaging spots as measurement spots or determining the evenly and discretely selected spots from the imaging spots as the measurement spots.

In the inspection device of the present invention, the object to be inspected is a stained specimen and the characteristics measurement unit measures spectral characteristics of the specimen. Also, the characteristics measurement unit has a multispectral sensor.

In the inspection device of the present invention, a measurement field of view of the measurement unit corresponds to a part of the imaging field of view of the imaging unit.

In the inspection device of the present invention, the imaging information includes any of imaging magnification or a number of imaging spots. The inspection information includes any of a facility where the object to be inspected was prepared, a staining method applied for the object, an organ type, a thickness, and image information. The measurement information includes any of channels used by a multispectral sensor provided in the characteristics measurement unit, integrating duration of the multispectral sensor, sensitivity of the multispectral sensor, integrating times.

BRIEF DESCRIPTION OF THE DRAWINGS

FIG. 8(a) is a diagram showing the inspection method of the inspection device of the third embodiment according to the present invention.

FIG. 8(b) is a diagram showing one measurement region existing area.

FIG. 8(c) is a diagram showing one measurement region existing area.

FIG. 9 is a diagram showing the measurement spot for the inspection device of the third embodiment according to the present invention.

DETAILED DESCRIPTION OF SPECIFIC EMBODIMENTS

Embodiments of inspection devices of the present invention will be described in detail hereinafter with reference to the drawings.

First Embodiment

The inspection device of the present invention can be applied in a variety of fields, for example, the inspection device can be utilized for the purposes of detecting particular colors and improving color reproducibility in image acquisition. In the present embodiment, for example, a pathological specimen derived from a block sample obtained by organ harvesting or a pathological specimen obtained by needle biopsy is used as an object to be inspected. The inspection device is described as a device conducting pathological inspection by imaging the pathological specimen and measuring characteristics thereof. A thin slice of a specimen generally stained with dye prior to observation, since the slice of the specimen hardly absorbs or scatters lights and is nearly clear and colorless.

Staining of a biological tissue specimen is a process of fixing dye to a biological tissue with inherent individual differences by using chemical reactions and uniform result is not obtained constantly. As a result, variation in staining usually occurs among specimens. In one facility, such variation in staining can be reduced by employing staining technicians having technical skills. However, the variation in staining between different facilities still remains.

Under the presence of staining variation, very important evidence may be overlooked. Also, in the case where the stained sample is imaged by a camera and subject to image processing, the precision level of image processing will be affected by the staining variation. For example, it is difficult to extract image areas corresponding to a specific lesion automatically from an observed image generated by imaging a specimen, even if the lesion was known to exhibit a specific color.

Figure 1:
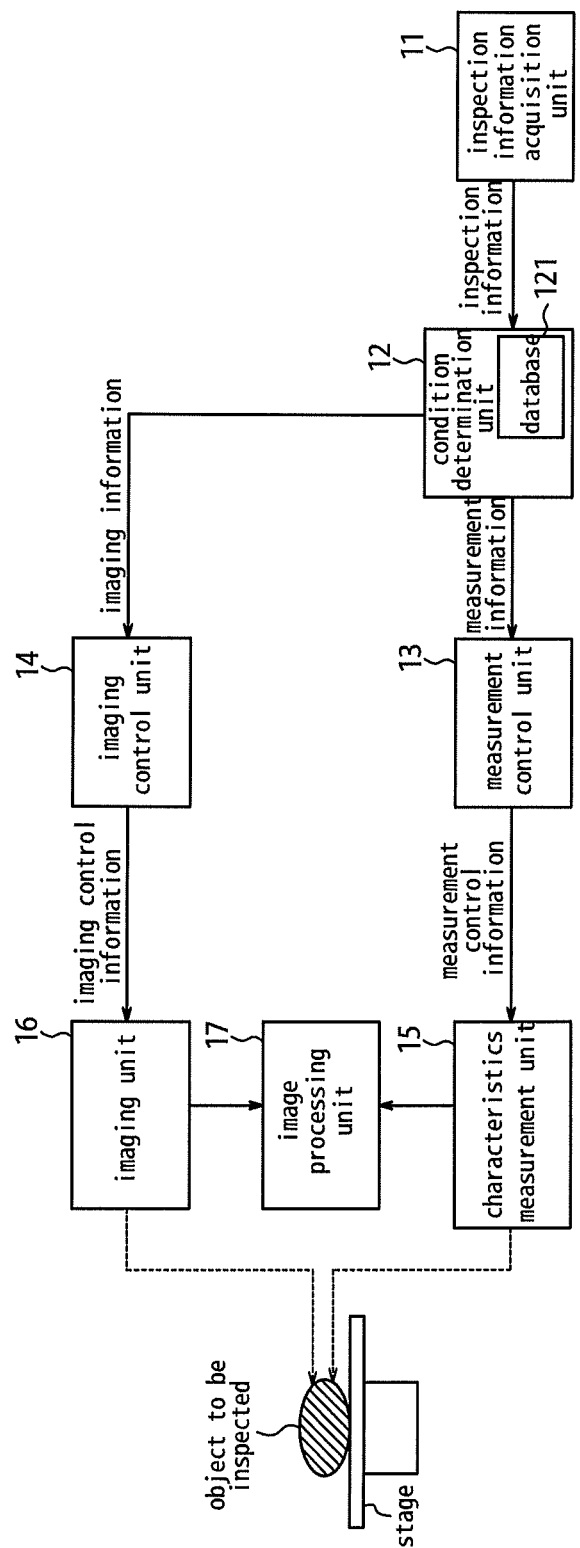
FIG. 1 is a block diagram showing configuration of the inspection device of the first embodiment according to the present invention.

Thus, the inspection device of the present embodiment acquires an image by imaging stained specimen, acquires a spectroscopic characteristics (spectral data) of the specimen, estimates amount of each dye within the specimen by executing arithmetic processing on image and spectroscopic characteristics of the specimen, corrects the amount of each dye by increasing and decreasing it arbitrarily, and generates image data based on the corrected amount of each dye so as to acquire an observed image FIG. 1 is a block diagram showing configuration of the inspection device of the first embodiment. The inspection device of the present embodiment comprises an inspection information acquisition unit 11, a condition determination unit 12, a measurement control unit 13, an imaging control unit 14, a characteristics measurement unit 15, an imaging unit 16, and an image processing unit 17.

The inspection information acquisition unit 11 receives input from user interface, acquires input inspection information related to an object to be inspected, and outputs it to the condition determination unit 12. The inspection information can be input manually by using a keyboard or by reading barcode having inspection information with a barcode reader.

The inspection information acquisition unit 11 preferably comprises an automatic reading type barcode reader. The automatic reading type barcode reader read barcode having the inspection information, when the specimen is set on a predetermined position. Accordingly, the device can acquire the inspection information in a fully automated fashion without receiving manual input. In this way, the device can acquire inspection information directly from the barcode. Alternatively, the device can acquire inspection information via a communication means such as the Internet, according to the information read by the barcode reader.

Inspection information, for example, includes information of a facility where the specimen was prepared, a staining method applied for the specimen, an organ type of the specimen, and a thickness of the specimen. One example of the inspection information is shown in Table 1. Other than the information, information of staining dye applied for the specimen and image information can be included.

TABLE 1

| Inspection information | Contents |
| --- | --- |
| Facility where the specimen was prepared | Hospital α, Hospital β, Hospital γ, . . . |
| Staining method applied for the specimen | Staining method 1, Staining method 2, Staining method 3, . . . |
| Organ type of the specimen | Organ A, Organ B, Organ C, . . . |
| Thickness of the specimen | Larger than a predetermined value, Smaller than a predetermined value |

The facility where the specimen was prepared refers to a name of the facility where the specimen was prepared. With regard to staining methods applicable for the specimen, variety of staining methods is suggested. With regard to a pathogenic specimen, hematoxylin-eosin staining (HE staining) which utilizes blue-violet hematoxylin and red eosin as dye is normally applied. FISH (Fluorescence In Situ Hybridization) and CISH (Chromogenic In Situ Hybridization) are known as methods for detecting chrosomomal aneuploidy and gene amplification related to cancer and genetic disorder. As the inspection information, "cutting out method of the organ" can be added. Also, in the case where the type of the specimen is the same, "cutting out method of the organ" can be substituted instead of "organ type of the specimen".

The condition determination unit 12 outputs imaging information which relates to imaging condition, among the inspection information input from the inspection information acquisition unit 11 to the imaging control unit 14 and outputs measurement information which relates to measurement condition to the measurement control unit 13. In the imaging information, for example, information of imaging magnification is included. One example of the imaging information is shown in Table 2. Please note that some systems can be operated according to a predetermined magnification only and the imaging information is unnecessary in this system.

TABLE 2

| Imaging information | Contents |
| --- | --- |
| Imaging magnification | x 10, x 20, x 40, . . . |

In the measurement information, information of measurement field of view, measurement spectral channels (measurement spectral CHs), integrating times, integrating duration of a spectral sensor, and presence of infrared cutting filter in front of spectral sensor is included. One example of the measurement information is shown in Table 3. Other than the above information, information of sensitivity of the spectral sensor can be included.

TABLE 3

| Measurement information | Contents |
| --- | --- |
| Measurement field of view | Squares of 100 μm, 400 μm, 1 mm, . . . |
| Measurement spectral CHs | 1-15 CHs, 1-12 CHs, odd CHs, . . . |
| Integrating times | 1, 3, 10, . . . times |
| Integrating duration of a spectral sensor | 3 times with different integrating durations, 5 times with different integrating durations |
| Presence of an infrared cutting filter | Yes/No |

Figure 2:
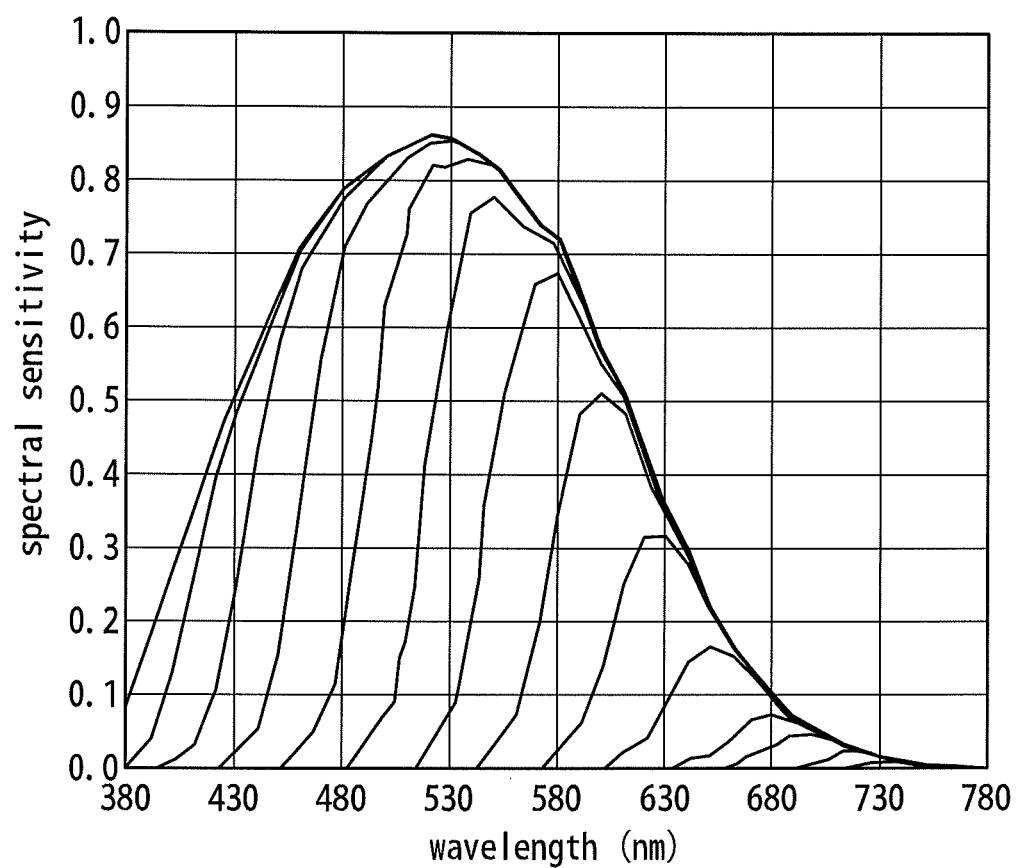
FIG. 2 is an example of spectral sensitivity of a multi spectral sensor.

The measurement field of view can be changed by switching frame of measurement field of view attached to the characteristics measurement unit 15. The measurement spectral channels correspond to spectral channels used for measurement among the spectral channels which can be measured by the multi-spectral sensor in the characteristics measurement unit 15. FIG. 2 shows an example of spectral sensitivity of a multi spectral sensor. The horizontal line shows wavelength and the vertical line shows spectral sensitivity. By using larger number of channels, the measurement accuracy will be improved. On the other hand, in the case where high accuracy is not necessary, the number of channels used is reduced and thus measurement duration can be shortened. The integrating time refers to a number of measurements for acquiring an average value based on a plurality of measurements. By increasing integrating time, higher accuracy of the measurement will be acquired and a dark object can be imaged. Also, by conducting measurement in a plurality of times with different integrating durations of the spectral sensor, a dynamic range can be broadened. The presence of infrared cutting filter means the presence of infrared cutting filter in front of the multi-spectral sensor.

The condition determination unit 12 comprises a database 121. The database 121 is a table connecting prepared inspection information, imaging information, and measurement information one-by-one. The condition determination unit 12 refers to the database 121 and determines measurement information, or measurement information and imaging information, corresponding to the inspection information input from the inspection information acquisition unit 11. The database 121 may also be configured as a table connecting only inspection information and measurement information one-by-one and acquires imaging information directly from the inspection information acquisition unit 11.

By connecting inspection information and measurement information, the optimal measurement condition for each of objects to be inspected can be determined. For example, spectrum of a specimen is different according to staining solution (and light source) and spectra necessary for measurement is different too. For example, in a condition where a light source with no infrared radiation and HE staining are applied together and spectra are used for estimation of amount of dyes, spectra over 600 nm close to infrared spectrum are insufficient in their light intensities and requires longer time for measurements. In such case, measurement time and data amount can be reduced by omitting spectra close to infrared spectra in measurements. Also, in the case where the inspection device is adapted to microscope, light level detected by a multi-spectral sensor is significantly low, depending on staining solution (and light source) and magnification level being set. In such case, integrating times in measurement will grow, since the data reliability may be deteriorated because of noise. One example of the database 121 is shown in Table 4.

TABLE 4

| | | | | | | | | |
|---|---|---|---|---|---|---|---|---|
| Specimen information | Facility where the specimen was prepared | Hospital α | | | | | | ... |
| | Staining method applied for the specimen | Staining method 1 | | | Staining method 2 | | | ... |
| | Organ type of the specimen | Organ A | Organ B | Organ C | Organ A | Organ B | Organ C | ... |
| | Thickness of the specimen | Smaller than a predetermined value | | | | | | ... |
| Imaging information | Imaging magnification | ×20 | | | | | | ... |
| Measurement information | Measurement field of view | 100 μm sq. | 400 μm sq. | 1 mm sq. | 100 μm sq. | 400 μm sq. | 1 mm sq. | ... |
| | Measurement spectral CHs | 1-12 CHs | | | 1-15 CHs | | | ... |
| | Integrating times | 1 | | | 10 | | | ... |
| | Integrating duration of a spectral sensor | 3 times with different integrating durations | | | 5 times with different integrating durations | | | ... |
| | Presence of an infrared cutting filter | None | | | None | | | ... |

The imaging control unit 14 generates imaging control information for controlling imaging of the object to be inspected by the imaging unit 16 based on the imaging information input form the condition determination unit 12 and outputs the generated imaging control information to the imaging unit 16.

The measurement control unit 13 generates measurement control information for controlling characteristics measurement by the characteristics measurement unit 15 based on measurement information input from the condition determination unit 12 and outputs the generated measurement control information to the characteristics measurement unit 15.

The characteristics measurement unit 15 measures spectral characteristics of the object to be inspected based on the measurement control information input from the measurement control unit 13 and outputs the measured data to the image processing unit 17.

The imaging unit 16 images the object to be inspected based on the imaging control information input from the imaging control unit 14 and outputs the image to the image processing unit 17.

The image processing unit 17 estimates the amount of each dye within the specimen by executing arithmetic processing on spectral characteristics input form the characteristics measurement unit 15 and the image input from the imaging unit 16. Then, the image processing unit 17 corrects the estimated amount of each dye by increasing and decreasing the estimated value arbitrarily, and generates image data based on the corrected amount of each dye so as to acquire an observed image with correction of staining condition. The actual method for this image processing is known (for Example, JP200914354) and this is not the main topic of the present application. Thus, the detailed illustration of the method is omitted.

Figure 3:
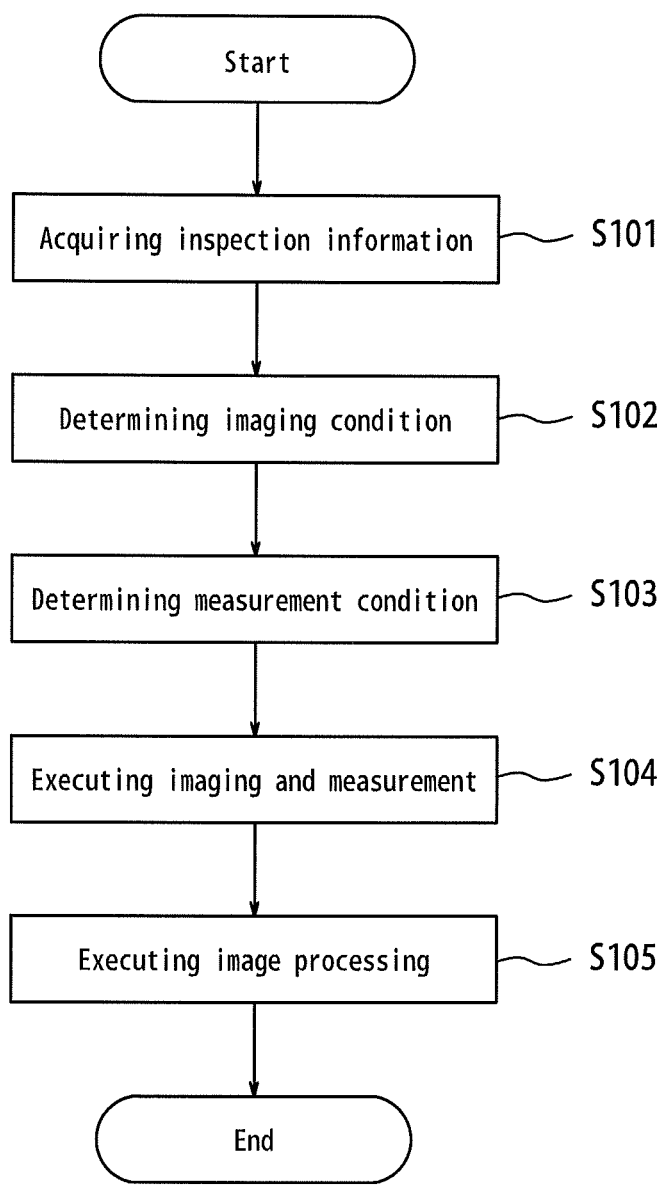
FIG. 3 is a flow chart showing operation of the inspection device of the first embodiment according to the present invention.

FIG. 3 is a flow chart showing operation of the inspection device of the present embodiment. The inspection device of the present embodiment acquires inspection information using the inspection information acquisition unit 11 (Step S101).

The inspection device determines imaging condition and measurement condition corresponding to the acquired inspection information by referring to the database 121 using the condition determination unit 12 (Step S102 and S103). Then, the inspection device images the object to be inspected and acquire an image using the imaging control unit 14 and the imaging unit 16 and measures the characteristics of the object to be inspected using the measurement control unit 13 and the characteristics measurement unit 15 so as to acquire measurement data (Step S104). Once the imaging and measurement of the object to be inspected has been finished, the inspection device executes image processing using the image processing unit 17 (step S105) and completes the inspection process. The inspection device can measure the spectral data of the illumination light illuminating the object to be inspected so as to conduct illumination calibration before step S101 or after step S105, if needed.

Thus, the inspection device of the first embodiment can conduct measurements under the optimal condition for each of objects to be inspected by varying measurement conditions according to type and feature of the object to be inspected using the condition determination unit 12.

Second Embodiment

The second embodiment of the present invention will be described in detail hereinafter with reference to the drawings. The components similar to those described in the first embodiment will be referenced by the same reference numbers and descriptions of those components will be arbitrarily omitted.

Figure 4:
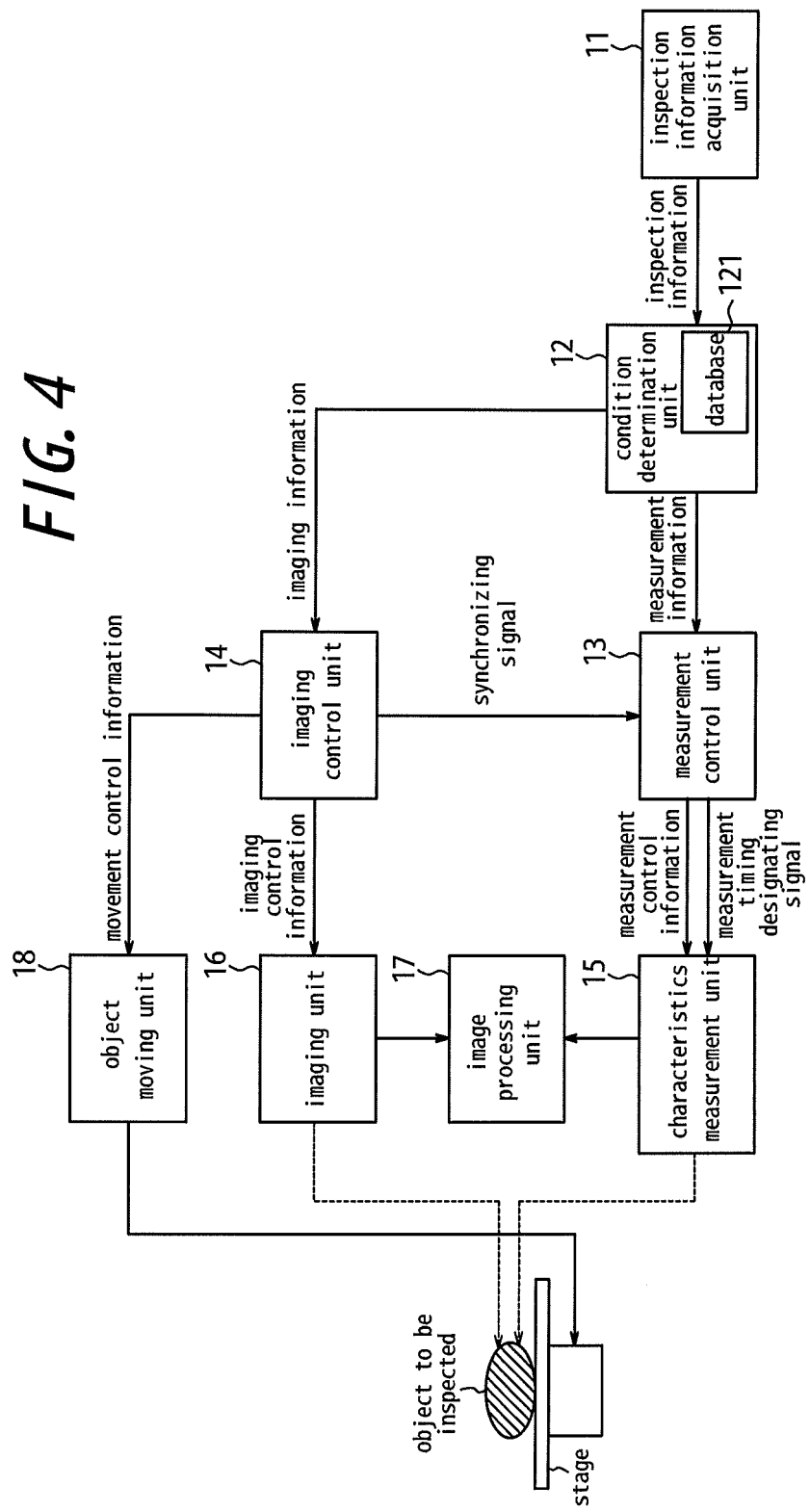
FIG. 4 is a block diagram showing configuration of the inspection device of the second embodiment according to the present invention.

FIG. 4 is a block diagram showing configuration of the inspection device of the second embodiment according to the present invention. The inspection device of the present embodiment comprises an inspection information acquisition unit 11, a condition determination unit 12, a measurement control unit 13, an imaging control unit 14, a characteristics measurement unit 15, an imaging unit 16, image processing unit 17, and a object moving unit 18. The inspection device of the present embodiment is different from the inspection device of the first embodiment (see FIG. 1) in the point where the device further comprises the object moving unit 18.

Figure 5:
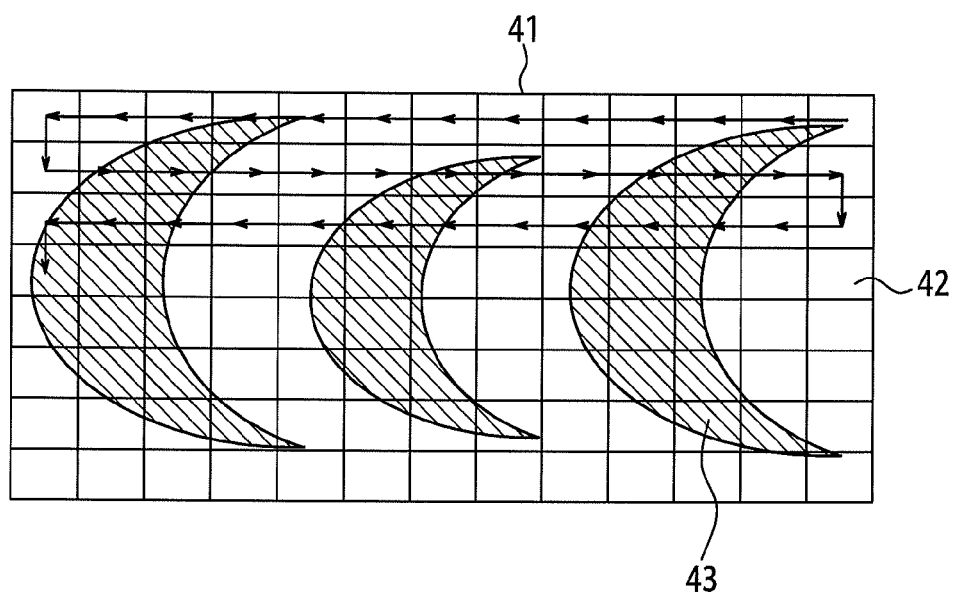
FIG. 5 is a diagram showing the inspection method of the inspection device of the second embodiment according to the present invention.

As shown in FIG. 5, the inspection device of the present embodiment images the object to be inspected with moving the object so as to acquire a plurality of divided images. That is, when conducting imaging with high magnification level, one divided imaging area 42 is smaller than the whole imaging area 41 and the stage carrying the object to be inspected is moved area-by-area having the size of divided imaging area 42 and then integrates the plurality of acquired images for acquiring the whole image of the imaging area 41. The range of one divided imaging area 42 corresponds to imaging range that can be imaged at one time. The arrows in FIG. 5 illustrate the order of imaging the divided imaging area(s) 42. The imaging information includes the number of imaging spot, since there is a plurality of imaging spots. Also, imaging can be conducted at some or all of the imaging spots. To this end, the measurement information includes information of the number of measurement spots and a way of selection of the measurement spots. The way of selection of the measurement spots is information represents which portion of the imaged spots to be select as measurement spot, or how to select the portion (for example, selecting spots evenly scattering all around or specifically selecting portions where many nuclei are found).

In accordance with the way of specimen acquisition and position of the acquired specimen, a ratio between areas with specimen (measurement region 43) and areas without specimen differs. Between areas with specimens, densities of nuclei and ratios between the areas with cytoplasm and the like (an area in measurement region 43 further including nuclei and cytoplasm) and empty areas are different according to the type of organ of the specimen. Within the area with the specimen, the pattern of the distribution and distribution density of the spots to be measured such as portions of nuclei and portions of cytoplasm are different.

Given that there are three kinds of specimens: specimen 1 which distributes evenly all around; specimen 2 which includes portions of dense nuclei and cytoplasm; specimen 3 which includes small areas of discrete nuclei and cytoplasm. Under such situation, in the case where a common measurement condition and a common way of selecting measurement spots are applied for acquiring spectral characteristics (spectral data) related to portions corresponding to stained nuclei and cytoplasm, the measurement condition and the way of selection will be adjusted to those of the worst one of the three and such measurement requires longer time and larger size of memory and thus inefficient. Specifically, in the case of measuring specimen 1, it is sufficient to measure several points of arbitrarily determined portion of the specimen or measuring discrete several points all around the specimen, while in the case of measuring specimen 3, few dozens of points of specimen are needed to be measured, since the area of nuclei and cytoplasm are small. In the specimen 2, the distribution of portions of nuclei and cytoplasm is uneven and if data measurement is conducted in an even or discrete fashion the number of measurement spots will increase and contrarily, the number of measurement spots can be decreased if the measurement was done selectively for the portions where nuclei and cytoplasm are close each other. The distribution pattern and the distribution density of these tissues differ according to the type of organ or cutting out method. Also, the size and shape of the nuclei differs according to the type of organs and etc. In the case where the nuclei are small and the field of view is large, it is impossible to measure spectra corresponding to the dye staining the nuclei.

Thus, in the present embodiment, precision and effectiveness of the measurement can be improved by database 121 which connects the type of organ, the number of measurement spots, and measurement field of view. In the present embodiment, the measurement condition is partly determined according to the type of organ, other information, such as cutting out method of the organ, can be utilized for the determination. One example of the imaging information is shown in Table 5, that of the measurement information is shown in Table 6, and that of database 121 is shown in Table 7.

TABLE 5

| Imaging information | Contents |
| --- | --- |
| Imaging magnification | x 10, x20, x40 . . . |
| Number of imaging spots | 50, 100, 1000, . . . |

TABLE 6

| Measurement information | Contents |
| --- | --- |
| Measurement field of view | 100 μm sq., 400 μm sq., 1 mm sq. |
| Measurement spectral CHs | 1-15 CHs, 1-12 CHs, Odd CHs, . . . |
| Integrating times | 1, 3, 10, . . . |
| Integrating duration of a spectral sensor | 3 times with different integrating, 5 times with different integrating durations |
| Presence of an infrared cutting filter | Yes/None |
| Number of measurement spots | 10, 30, 100, 500, . . . |
| Way of selecting measurement spots | Evenly, Selectively |

TABLE 7

| | | | | | | | | |
| --- | --- | --- | --- | --- | --- | --- | --- | --- |
| Specimen information | Facility where the specimen was prepared | Hospital α | | | | | | . . . |
| | Staining method applied for the specimen | Staining method 1 | | | Staining method 2 | | | . . . |
| | Organ type of the specimen | Organ A | Organ B | Organ C | Organ A | Organ B | Organ C | . . . |
| | Thickness of the specimen | Smaller than a predetermined value | | | | | | . . . |
| Imaging information | Imaging magnification | x20 | | | | | | . . . |
| | Number of imaging spots | 100 | | | | | | . . . |

TABLE 7-continued

| Measurement information | | 100 μm sq. | 400 μm sq. | 1 mm sq. | 100 μm sq. | 400 μm sq. | 1 mm sq. | ... |
|---|---|---|---|---|---|---|---|---|
| Measurement information | Measurement field of view | 100 μm sq. | 400 μm sq. | 1 mm sq. | 100 μm sq. | 400 μm sq. | 1 mm sq. | ... |
| | Measurement spectral CHs | | 1-12 CHs | | | 1-15 CHs | | ... |
| | Integrating times | | 1 | | | 10 | | ... |
| | Integrating duration of a spectral sensor | | 3 times with different integrating | | | 5 times with different integrating durations | | ... |
| | Presence of an infrared cutting filter | | None | | | None | | ... |
| | Number of measurement spots | 10 | 10 | 50 | 10 | 10 | 50 | ... |
| | Way of selecting measurement spots | Evenly | Selectively | Evenly | Evenly | Selectively | Evenly | |

Figure 15:
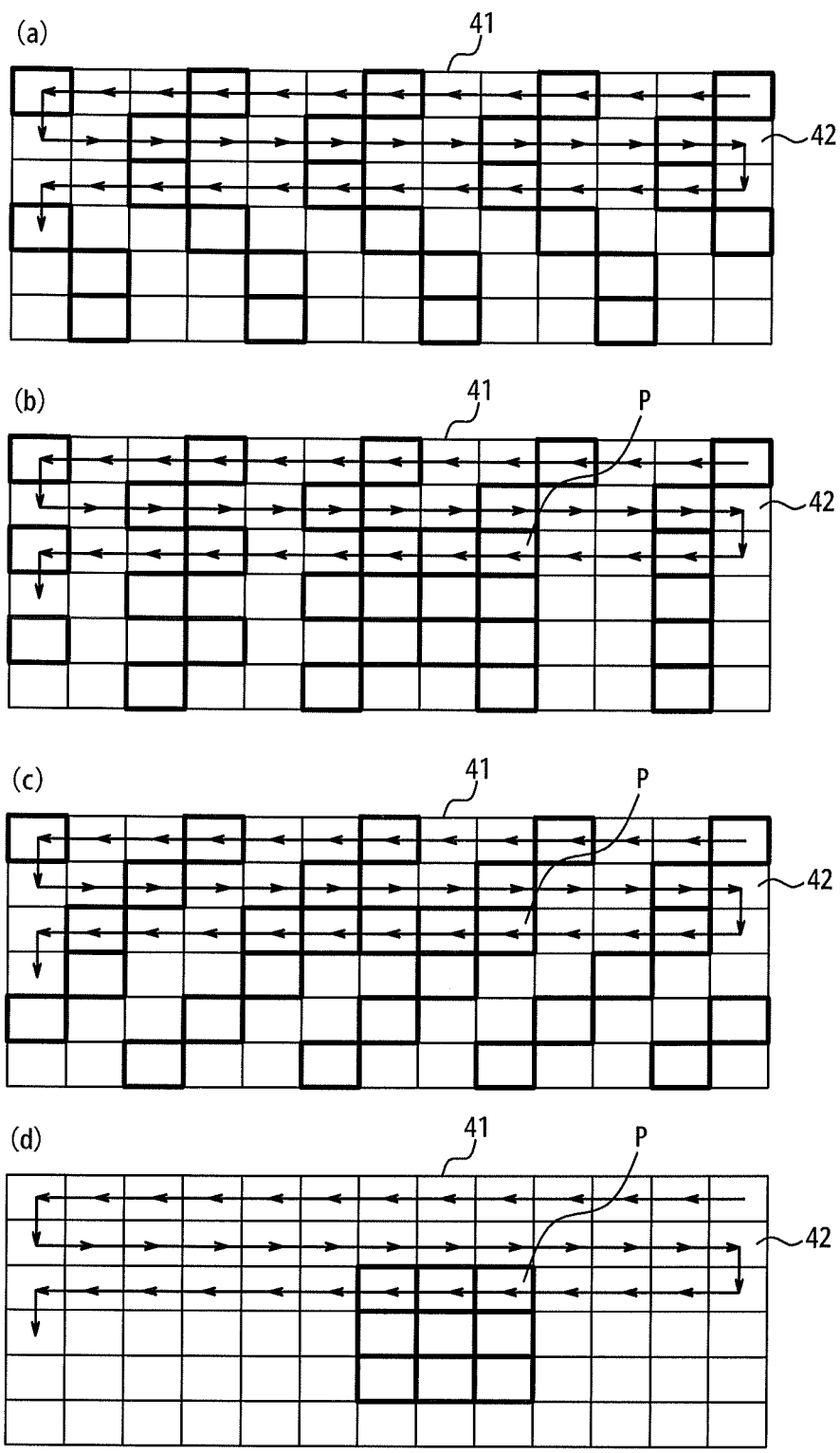
FIG. 15(a) shows measurement spots in an imaging area for the inspection device of the second embodiment of the present invention.
FIG. 15(b) shows measurement spots in an imaging area for the inspection device of the second embodiment of the present invention.
FIG. 15(e) shows measurement spots in an imaging area for the inspection device of the second embodiment of the present invention.
FIG. 15(d) shows measurement spots in an imaging area for the inspection device of the second embodiment of the present invention.

FIG. 15 shows measurement spots in an imaging area. For example, in the case where "evenly" is selected as the way of selecting measurement spots, the ratio between the number of imaging spots and the number of measurement spots can be set as k. Under such setting, measurements will be conducted once in k times of imaging. FIG. 15(a) shows allocation of the measurement spots represented by bold rectangles in the case where the ratio k is set as 3, in the case where all the divided imaging areas 42 are set as imaging spots. In the case where "selective" is selected as the way of selecting measurement spots, measurements will be conducted once in 1 times of imaging and if measured data for a certain measurement spot shows predetermined pattern, such as a pattern that shows high intensity of specific wavelength, intensive measurements will start with the measurement spot. For example, a measurement for m×n divided imaging areas 42 will start from the measurement spot P, or measurement and imaging for adjacent n divided imaging areas 42 will start form the measurement spot P (here, l, m, n may be set as any integers). FIG. 15(b) shows allocation of the measurement spots represented by bold rectangles in the case where the ratio 1 is set as 3 and m is set as 3, in the case where all the divided imaging areas 42 are set as imaging spots. FIG. 15(c) shows allocation of the measurement spots represented by bold rectangles in the case where the ratio 1 is set as 3 and n is set as 5, in the case where all the divided imaging areas 42 are set as imaging spots. Also, in the case where "selective" is selected as the way of selecting measurement spots, the measurement can be conducted only within the predetermined area of the divided imaging areas 42 represented by a bold rectangular and can be started from the measurement spot P.

The imaging control unit 14 generates imaging control information for controlling the imaging of the object to be inspected based on the imaging information input from the condition determination unit 12, outputs the generated imaging control information to the imaging unit 16, generates movement control information for controlling the position of the object to be inspected, and outputs the generated movement control information to the object moving unit 18. Also, the imaging control unit 14 outputs synchronizing signals to the measurement control unit 13 for synchronizing the imaging conducted by the imaging unit 16 and the measurement conducted by the characteristics measurement unit 15, in the case where the imaging spot and the measurement spot correspond to each other.

The measurement control unit 13 generates measurement control information for controlling the characteristics measurement conducted by the characteristics measurement unit 15 and outputs the measurement control information to the characteristics measurement unit 15. Also, the measurement control unit 13 generates measurement timing designating signals based on the synchronizing signals input from the imaging control unit 14 and outputs the measurement timing designating signals to the characteristics measurement unit 15.

The image processing unit 17 has a function of integrating the divided images input form the imaging unit 16.

The object moving unit 18 controls the position of the object to be inspected based on the movement controlling information input form the imaging control unit 14. For example, in the case where the object to be inspected is placed on the stage or a line, the object moving unit 18 controls the position of the object to be inspected by moving the stage or the line.

Figure 6:
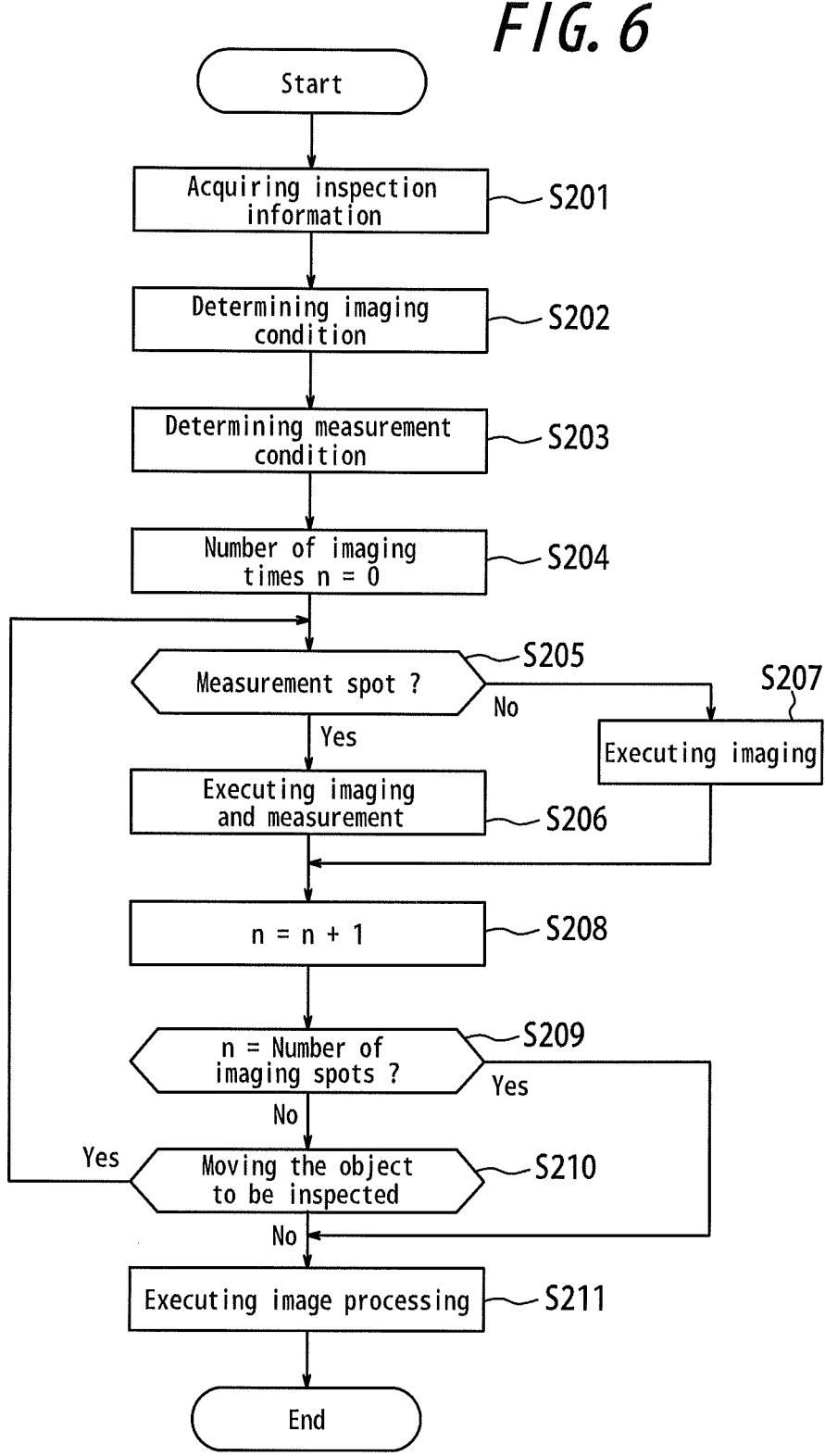
FIG. 6 is a flowchart showing an operation of the inspection device of the second embodiment according to the present invention.

FIG. 6 is a flowchart showing an operation of the inspection device of the present embodiment. The inspection device of the present embodiment acquires inspection information by using the inspection information acquisition unit 11 (step S201). Then, the inspection device determines the imaging condition and measurement condition corresponding to the acquired inspection information by referring to the database 121 by using the condition determination unit 12 (steps S202 and S203).

The imaging control unit 14 sets the number of imaging times n as default value zero, since the inspection device of the present embodiment conducts imaging for a plurality of spots (step S204). The imaging control unit 14 determines whether the imaging spot corresponding to a measurement spot (step S205). In the case where the imaging spot corresponds to a measurement spot, the inspection device conducts imaging of the object to be inspected by using imaging unit 16 and conducts measurement of the object simultaneously with the imaging by using the characteristics measurement unit 15 (step S206). On the other hand, in the case where the imaging spot does not correspond to the measurement spot, the inspection device just conducts imaging of the object to be inspected by using imaging unit 16 (step S207). After the processing in the steps S206 and S207, the imaging control unit 14 increments the number of imaging times n by one (step S208).

Then, the control unit 14 determines whether the number of imaging times n corresponds to the number of imaging spots designated by the imaging information (step S209). In the case where the number of imaging times n does not correspond to the number of imaging spots, the object to be inspected is moved by the object moving unit 18 (step S210) and the processing executed in steps S205 to S209 is repeated. On the other hand, in the case where the number of imaging times n corresponds to the number of imaging spots, the inspection device executes image processing by using the image processing unit 17 (step S211) and completes the inspection process.

As mentioned above, according to the inspection device of the second embodiment, the measurement is conducted in synchronization with the acquisition of the divided images of the object to be inspected and the measurement is repeated up to the necessary number of measurement times. Thus, the inspection device of the second embodiment can save inspection time and can utilize smaller size memory for storing measurement result, compared to the case where the position of the object is controlled after imaging and conducts measurement or the case where the measurement is conducted at every imaging.

Third Embodiment

The third embodiment of the present invention will be described in detail hereinafter with reference to the drawings. The components similar to those described in the second embodiment will be referenced by the same reference numbers and descriptions of those components will be arbitrarily omitted.

Figure 7:
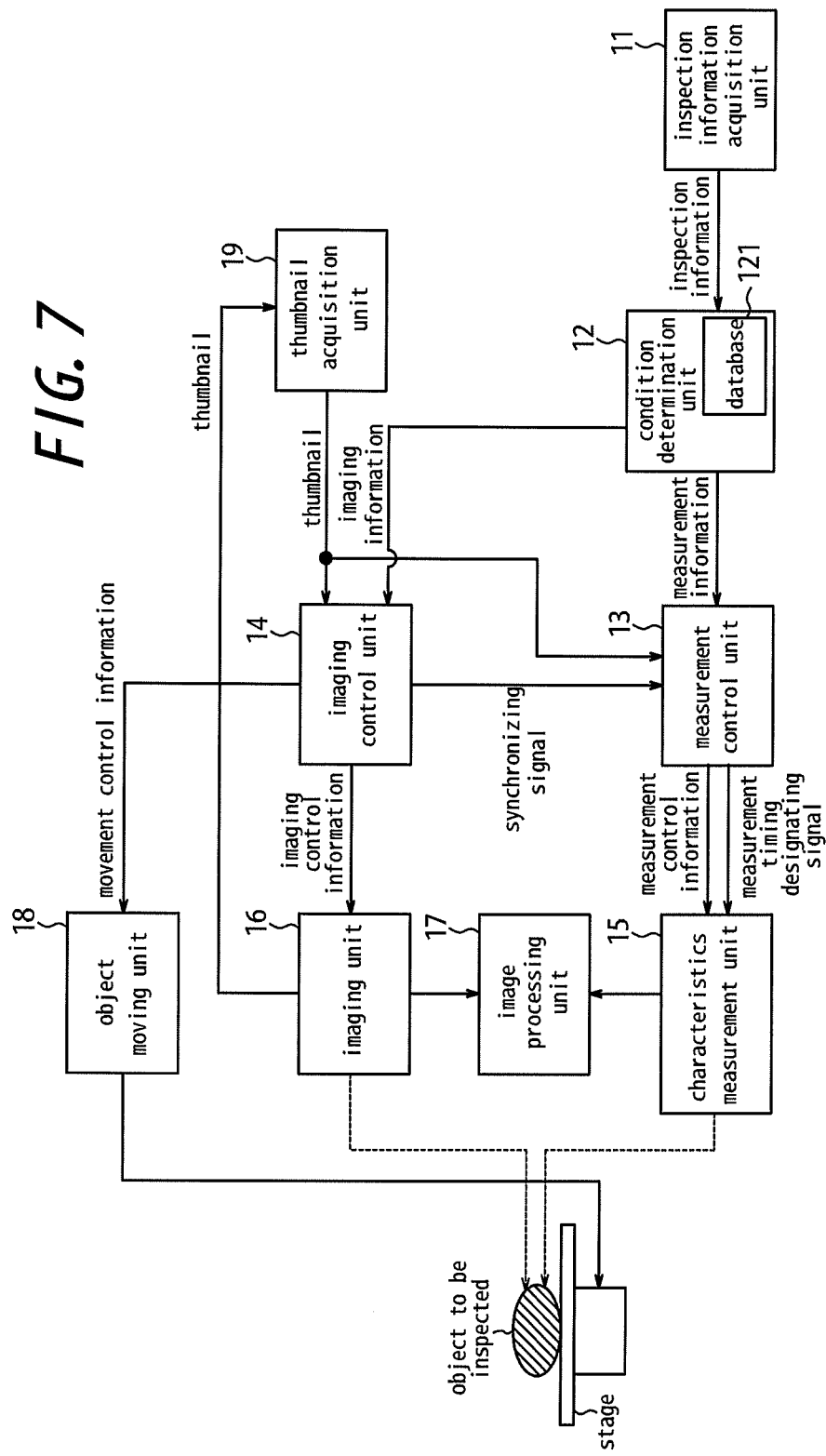
FIG. 7 is a block diagram showing configuration of the inspection device of the third embodiment according to the present invention.

FIG. 7 is a block diagram showing configuration of the inspection device of the third embodiment according to the present invention. The inspection device of the present embodiment includes the inspection information acquisition unit 11, the condition determination unit 12, the measurement control unit 13, the imaging control unit 14, the characteristics measurement unit 15, the imaging unit 16, the image processing unit 17, the object moving unit 18, and a thumbnail acquisition unit 19. The inspection device of the present embodiment is different from the inspection device of the second embodiment (see FIG. 4) in the point where the device further comprises the thumbnail acquisition unit 19. The imaging unit 16 may be provided with the thumbnail acquisition unit 19.

The thumbnail acquisition unit 19 images the whole image of the object to be inspected by the imaging unit 16 so as to acquire low magnification whole images (referred to as "thumbnails" hereinafter) before conducting the imaging and measurement of the object to be inspected and outputs the acquired thumbnails to the measurement control unit 13 and the imaging control unit 14.

The imaging control unit 14 acquires location information of measurement regions in the object to be inspected based on the thumbnail received from the thumbnail acquisition unit 19. Then, the imaging control unit 14 generates movement control information for controlling the location of the object to be inspected so as to control the imaging unit 16 to image only the portions including the measurement spots and outputs the generated movement control information to the object moving unit 18. By moving the object to be inspected by the object moving unit 18, the imaging unit 16 can image only the measurement region existing areas 44, the portions in the divided imaging areas 42 including the measurement region 43, as shown in FIG. 8(a). The arrows in FIG. 8(a) represent the order of imaging the measurement region existing areas 44.

A user of the inspection device can understand the position of the measurement region 43 in the imaging area precisely by referring to the thumbnails. Thus, the way of selecting measurement spot can be set as, for example, "evenly in the specimen region" or "evenly except for the region within 1 mm from the edge of specimen", while the way is set as "evenly" or "selectively" in the second embodiment. In the present embodiment, the measurement spots can be designated in the measurement region 43 and in the inner area of the measurement region 43 of the imaging region.

In the present embodiment, the measurement area 45 is located in the center of the measurement region existing area 44, since the measurement field of view is narrower than the imaging field of view. Also, imaging spots including measurement regions 43 at least in a part of the measurement area 45, preferably in the whole area of the measurement area 45 can be designated as a candidate spot for measurement, since precise information can be acquired from the thumbnail. FIGS. 8(b) and 8(c) show one measurement region existing area 44, which is cut out from the imaging area 41 shown in FIG. 8(a). The measurement area 45 in the FIG. 8(b) includes no measurement region 43 and the corresponding imaging spot is not designated as the candidate spot for measurement. On the other hand, the measurement area 45 in FIG. 8(c) includes measurement region 43 and the corresponding imaging spot is designated as the candidate spot for measurement. In this way, further unnecessary measurement can be avoided.

In some cases sufficient number of measurement spots designated by the measurement information are not available, under certain situation, such as a situation where the number of measurement region existing areas 44 for the imaging area is relatively small. In such cases, taking into account the case where the number of candidate spots for measurement is insufficient, at least two spots can be measured for one imaging spot so as to add measurement spots. FIG. 9 illustrates the addition of the measurement spots and shows one imaging spot (measurement region existing area 44), which is cut out from the imaging area 41 shown in FIG. 8(a). A measurement area 45a represents the measurement spot in the measurement region existing area 44. In the case where the number of measurement spots is insufficient, the measurement area 45b is set at a position displaced by a predetermined distance within the same measurement region existing area 44, since the measurement field of view for the measurement area 45a is smaller than the measurement region existing area 44. In the case where the measurement region 43 extends at least in a part or in the whole area within the measurement area 45b, the measurement area 45b will be added as the second candidate spot for measurement. In order to conduct measurement of the measurement area 45b, the object to be inspected can be controlled to move to a location away by predetermined distance with respect to the measurement region existing area 44 in FIG. 9 and as a result, the measurement area 45b will correspond to a measurement area of the sensor.

Figure 10:
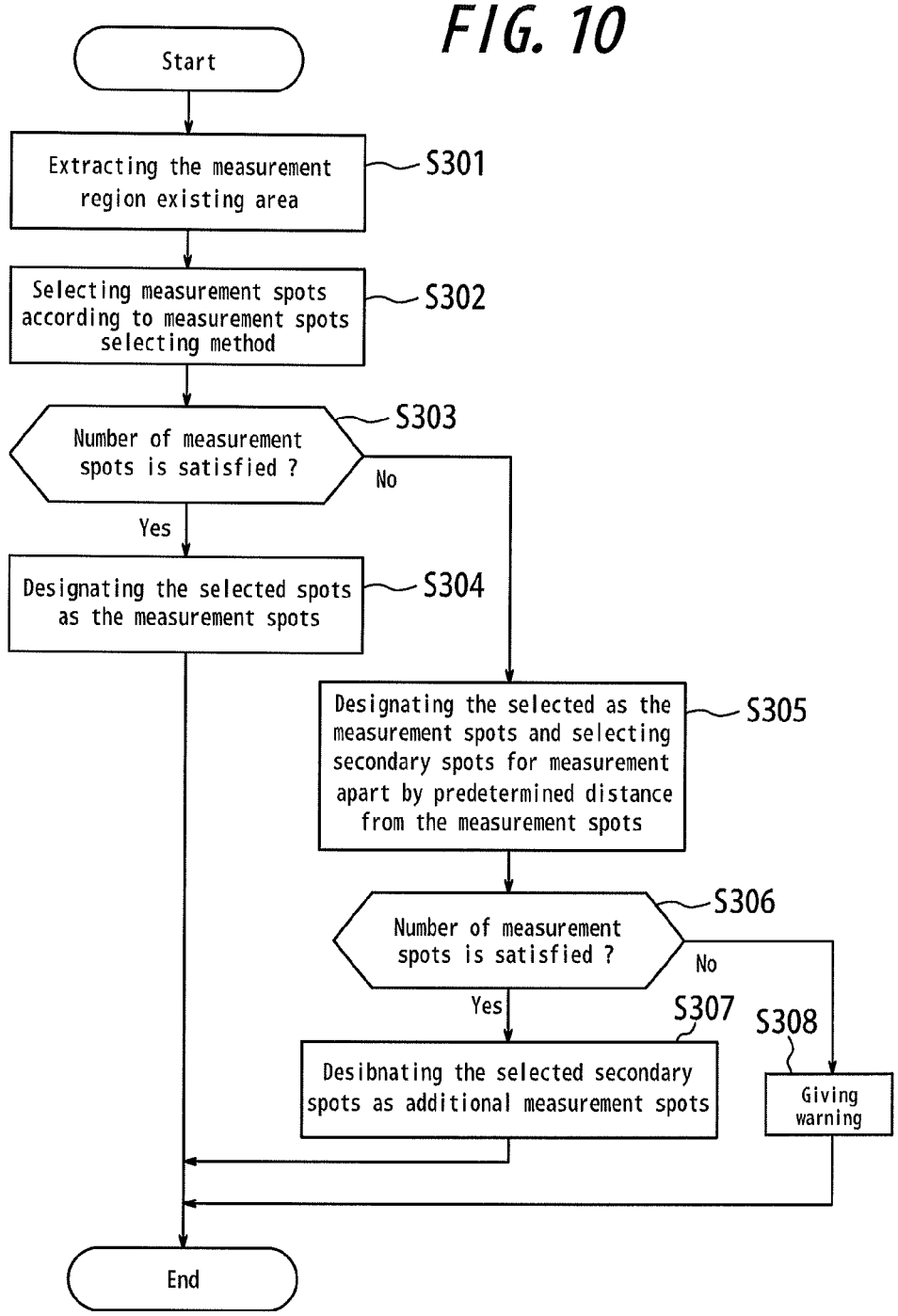
FIG. 10 is a flow chart illustrating the way of selecting the measurement spots in the third embodiment of the present invention.

FIG. 10 is a flow chart illustrating the way of selecting the measurement spots by the measurement control unit 13. First, the measurement control unit 13 acquires size information of the divided imaging area 42 from the imaging control unit 14 and divides the imaging area into the plurality of divided imaging area 42 based on thumbnail and extracts the measurement region existing area 44 (step S301). Then, the measurement control unit 13 selects the measurement spots among the candidate spots for measurement according to the measurement spots selecting method designated by measurement information (step S302), and determines whether the number of measurement spots designated by the measurement information is satisfied or not (step S303). In the case where a sufficient number of measurement spots, satisfying the number of measurement spots, are selected, the measurement control unit 13 designates the selected spots as the measurement spots (step S304).

On the other hand, in the case where the measurement control unit 13 fails to select sufficient number of measurement spots, satisfying the number of measurement spots, the selected spots will be designated as the measurement spots and selects secondary candidate spots for measurement apart by predetermined distance from the measurement spots (step S305). Then, the measurement control unit 13 again determines whether sufficient number of measurement spots are selected or not (step S306). In the case where the sufficient number of measurement spots are selected, the measurement control unit 13 designates the secondary candidate spots for measurements as additional measurement spots (step S307). On the other hand, in the case where the measurement control unit 13 fails to select the sufficient number of the measurement points, satisfying the number of measurement points, the measurement control unit 13 gives a warning (step S308). In the case where a display unit attached to the inspection device, the device can be configured to display a message for providing options for a user whether executing measurements with less measurement spots than the number designated by the measurement information or to display a message encourage the user to determine whether to replace the object to be inspected or not and to execute processing according to the selected method.

Figure 11:
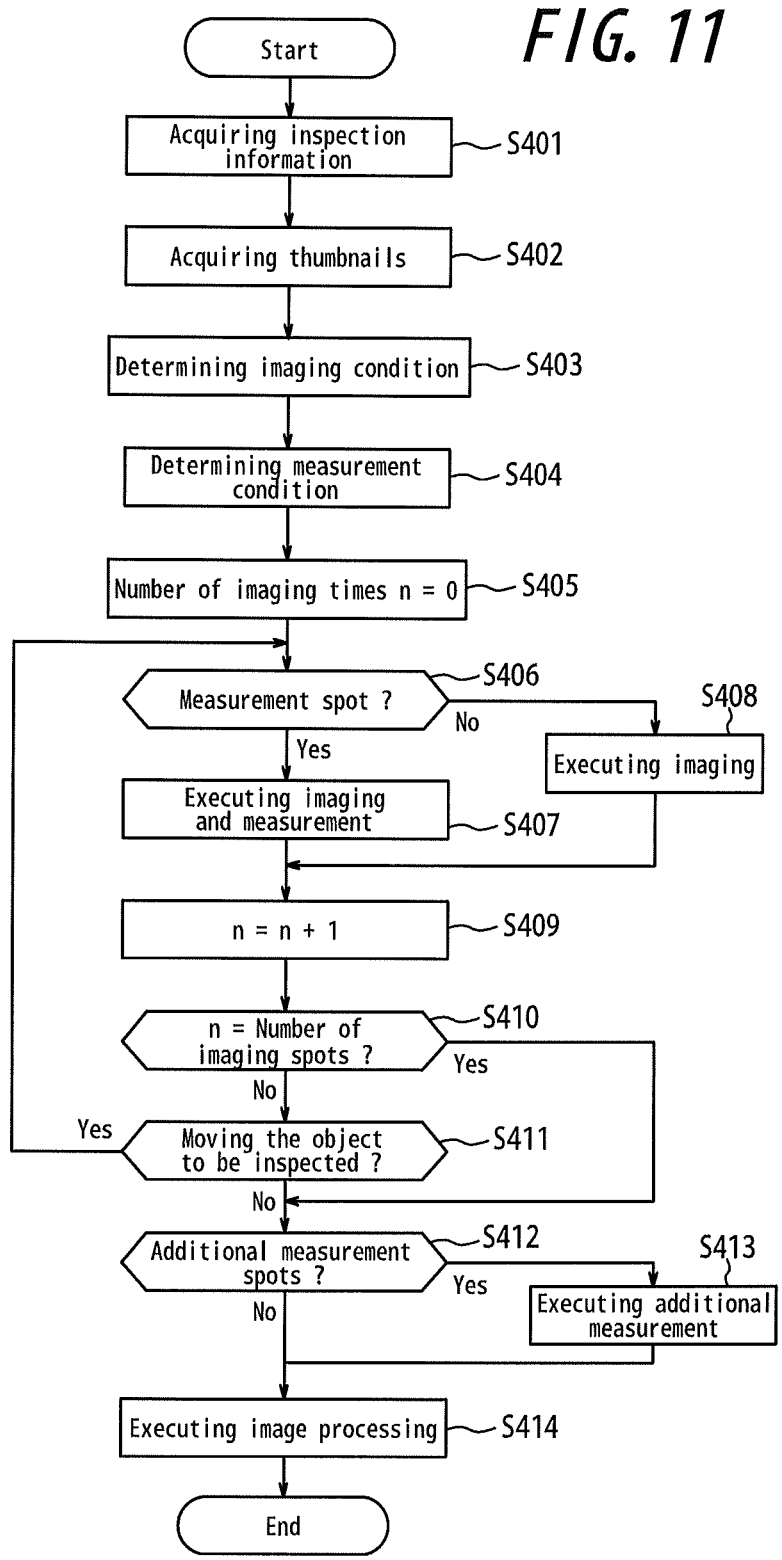
FIG. 11 is a flow chart illustrating operation of the inspection device of the third embodiment according to the present invention.

FIG. 11 is a flow chart illustrating operation of the inspection device of the present embodiment. The inspection device of the present embodiment acquires the inspection information by the inspection information acquisition unit 11 (step S401), and acquires thumbnail of the imaging area by the thumbnail acquisition unit 19 (step S402). Then, the inspection device accesses the database 121 and determines the imaging condition and measurement condition corresponding to the acquired inspection information by using the condition determination unit 12 (steps S403 and S404).

The imaging control unit 14 sets the number of imaging times n as default value zero (step S405). The imaging control unit 14 determines whether the imaging spot corresponds to the measurement spot or not (step S406). In the case where the imaging spot corresponds to the measurement spot, the inspection device images the object to be inspected by the imaging unit 16 as well as conducts a measurement of the object to be inspected synchronously by the characteristics measurement unit 15 (step S407). On the other hand, in the case where the imaging spot does not correspond to the measurement spot, the inspection device just conducts imaging of the object to be inspected by the imaging unit 16 (step S408). After the processing in the steps S407 and S408, the imaging control unit 14 increments the number of imaging times n by one (step S208).

Then, the control unit 14 determines whether the number of imaging times n corresponds to the number of imaging spots designated by the imaging information (step S410). In the case where the number of imaging times n does not correspond to the number of imaging spots, the inspection device moves the object to be inspected by the object moving unit 18 (step S411) and repeats the processing executed in steps S406 to S410. On the other hand, in the case where the number of imaging times n corresponds to the number of imaging spots, the inspection device determines whether the additional measurement spots are included or not (step S412). In the case where the additional measurement spots are not included, image processing will be executed by image processing unit 17 (step S414) and the inspection process is completed. On the other hand, in the case where some additional measurement spots are included, the inspection device conducts measurements for the additional measurement spots by the characteristics measurement unit 15 (step S413). No imaging is conducted in the step S413. Then, the inspection device executes image processing by the image processing unit 17 (step S414) and completes the inspection process.

In the case where "evenly" is selected as the way of selecting measurement spots and ratio between the number of imaging spots and the number of measurement spots equals 1 (the number of imaging spots/the number of measurement spots=1), measurements will always be conducted synchronically with execution of imaging. Thus, the steps S406 and S408 can be omitted. In this case, measured data will be examined in every measurement and the measurement will be finished at the point of the number of measurement spots is satisfied and in the case where the amount of acquired measured data is insufficient, the additional measurement will be executed without conducting synchronous imaging. Otherwise, the amount of measurement data is checked whether the number of measurement spots is satisfied or not at the point of finishing imaging and the additional measurement will be executed in the case where the amount of the measured data is insufficient.

As mentioned above, according to the inspection device of the third embodiment, thumbnails are acquired preliminarily and no imaging and measurement are executed at the spots that do not include any measurement region. Thus, the inspection device of the third embodiment can save inspection time and can utilize smaller size memory for storing measurement result.

Fourth Embodiment

The fourth embodiment of the present invention will be described in detail hereinafter with reference to the drawings. The components similar to those described in the third embodiment will be referenced by the same reference numbers and descriptions of those components will be omitted.

Figure 12:
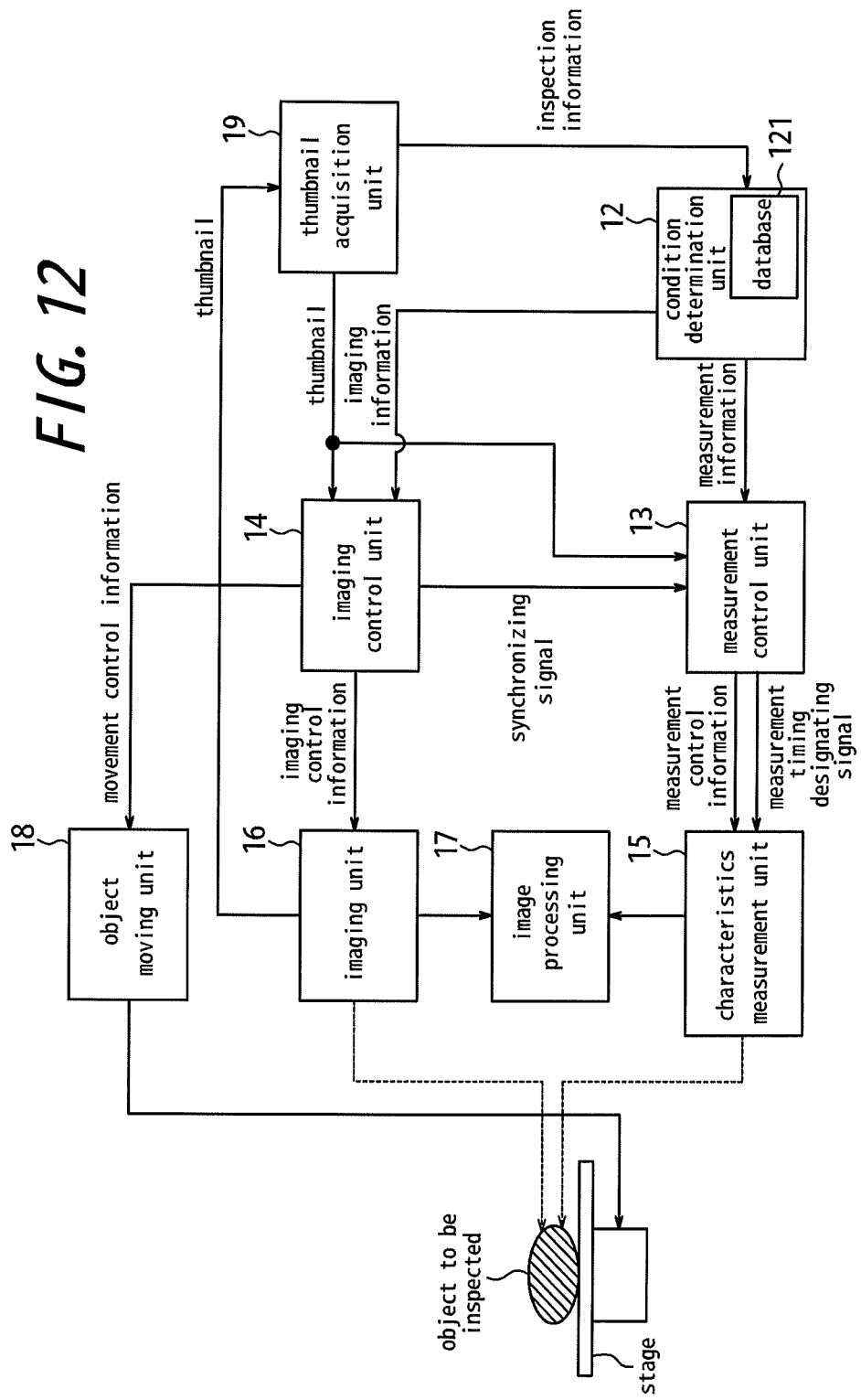
FIG. 12 is a block diagram showing configuration of the inspection device of the fourth embodiment according to the present invention.

FIG. 12 is a block diagram showing configuration of the inspection device of the fourth embodiment according to the present invention. The inspection device of the present embodiment includes the condition determination unit 12, the measurement control unit 13, the imaging control unit 14, the characteristics measurement unit 15, the imaging unit 16, the image processing unit 17, the object moving unit 18, and a thumbnail acquisition unit 19. The inspection device of the present embodiment is different from the inspection device of the third embodiment (see FIG. 7) in the point where the device does not include the inspection information acquisition unit 11.

The thumbnail acquisition unit 19 images the imaging area by imaging unit 16 so as to acquire thumbnails, before conducting imaging and measurement of the object to be inspected, outputs the acquired thumbnails to the measurement control unit 13 and imaging control unit 14 while generating the inspection information based on the acquired thumbnails, and outputs the generated inspection information to the condition determination unit 12. In this case, the inspection information includes average color information of each divided imaging areas 42 after white balance (WB) adjustment. Table. 8 shows one example of inspection information. Instead of the average color information of each divided imaging areas 42 after WB adjustment, average color information of the measurement region existing areas 44 of the specimen after WB adjustment can be employed.

TABLE 8

| Inspection information | Contents |
| --- | --- |
| Color information of each divided imaging area of the specimen after the WB adjustment | Area 1, Y = *** Cr = *** Cb = *** <br> Area 2, Y = *** Cr = *** Cb = *** <br> : <br> : |

The inspection information includes staining concentration and average color information of each divided imaging areas 42 after WB adjustment. Based on this information, for example, "areas of red hue" can be distinguished as areas having Cr value higher than or equal to a predetermined value and "areas of high concentration" can be distinguished areas having Y value less than or equal to a predetermined value. One example of the measurement information is shown in FIG. 9.

TABLE 9

| Measurement information | Contents |
| --- | --- |
| Number of measurement spots | 10, 30, 100, 1000, . . . |
| Measurement field of view | 100 μm sq., 400 μm sq., 1 mm sq. |
| Measurement spectral CHs | 1-15 CHs, 1-12 CHs, Odd CHs, . . . |
| Integrating times | 1, 3, 10, . . . |
| Integrating duration of a spectral sensor | 3 times with different integrating, 5 times with different integrating durations |
| Way of selecting measurement spots | Randomly, Selectively for areas having red hue, Selectively for areas having high concentration |

The operation in the fourth embodiment is different from that of the third embodiment in FIG. 11 in the point where the process of acquiring the inspection information (step S401) is unnecessary. Other steps following the step are the same.

In this way, according to the inspection device of the fourth embodiment, the thumbnail acquisition unit 19 generates the inspection information from the thumbnails and the input of the inspection information by a user becomes unnecessary and the process of inspection can be fully automated.

Figure 13:
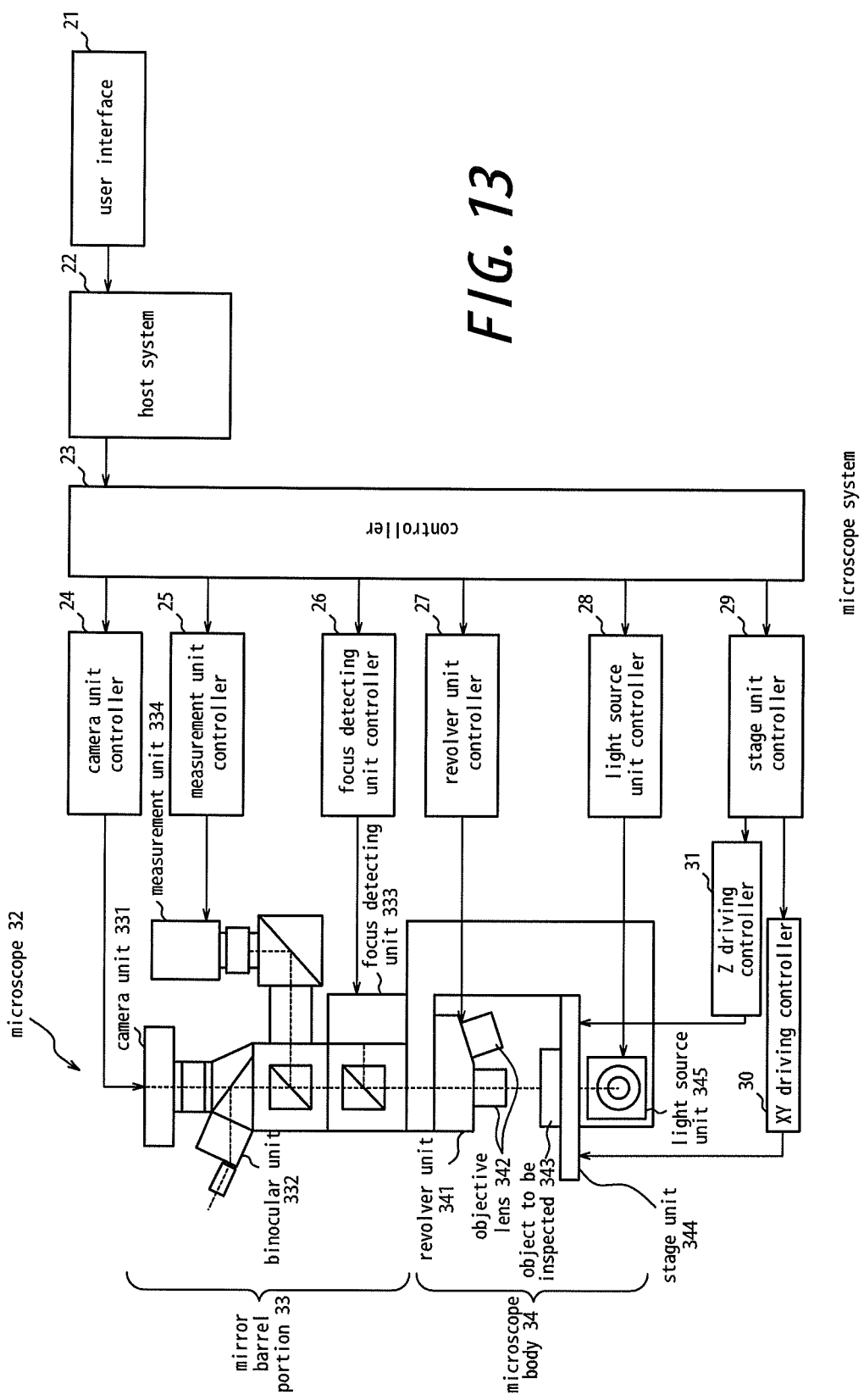
FIG. 13 shows a constitution of microscope system employing inspection device according to the third embodiment.

FIG. 13 shows a constitution of microscope system employing inspection device according to the third embodiment. The microscope system includes a user interface 21, a host system 22, a controller 23, a camera unit controller 24, a measurement unit controller 25, a focus detecting unit controller 26, a revolver unit controller 27, a light source unit controller 28, a stage unit controller 29, a XY driving controller 30, Z driving controller 31, and a microscope 32.

The user interface 21 corresponds to the inspection information acquisition unit 11. The host system 22 may be a PC and corresponds to the condition determination unit 12 and the image processing unit 17. The controller 23 corresponds to the measurement control unit 13 and the imaging control unit 14. The camera unit controller 24, the focus detecting unit controller 26, the revolver unit controller 27, and the light source unit controller 28 correspond to the imaging unit 16 and the thumbnail acquisition unit 19. The measurement unit controller 25 corresponds to the characteristics measurement unit 15. The stage unit controller 29, a XY driving controller 30, and Z driving controller 31 correspond to the object moving unit 18.

The microscope 32 includes a microscope body 34 having reversed C shape side view, mirror barrel portion 33 placed on the top of the microscope body 34. The mirror barrel portion 33 includes a camera unit 331, a binocular unit 332, a focus detecting unit 333, and a measurement unit 334. The camera unit 331 has image pickup devices such as CCD and CMOS imaging specimen placed within a field of view of the objective lens 342, images the object to be inspected, and outputs the image of the object to be inspected to the host system 22. The binocular unit 332 enables visual observation of the object to be inspected 343 by leading observation light. The measurement unit 334 acquires spectral information of the object to be inspected 343 and outputs the information to the host system 22.

The microscope body 34 includes a revolver unit 341 holding the objective lens 342, a stage unit 344 with the object to be inspected 343, and a light source unit 345 attached to the microscope body 34 at the back side of the bottom.

The revolver of the revolver unit 341 is rotatable with respect to the microscope body 34 and positions the objective lens 342 above the object to be inspected 343. The objective lens 342 are attached to the revolver with other objective lenses of different magnification level (magnification of observation) and can be exchanged with these and other objective lenses. One of the objective lens 342 is arranged in the light path of the observation light when the revolver is rotated and the objective lens 342 utilized for the observation of the object to be inspected 343 is alternatively switched.

Given that the direction of optical axis of the objective lens 342 is Z direction and a plane perpendicular to the Z direction is XY plane, the stage of the stage unit 344 is configured to move freely in the XYZ direction. That is, the stage can moves freely in the XY plane by a motor (not shown) and the XY driving controller 30 controlling the driving of the motor. The XY driving controller 30 detects the predetermined original point of the stage in the XY plane by an original point sensor (not shown) for XY positioning, determines the location of the original point, and controls the driving amount of the motor so as to move the observation field of view for the object to be inspected.

Also, the stage can be moved freely in the Z direction by a motor (not shown) and the Z driving controller 31 controlling the driving of the motor. The Z driving controller 31 detects the predetermined original point of the stage in the Z direction by an original point sensor (not shown) for Z positioning, determines the location of the original point, and controls the driving amount of the motor so as to move the object to be inspected to any Z location within a predetermined height range for focusing.

The controller 23 conducts overall control for each units consisting the microscope 32 based on the control of the host system 22. For example, the controller 23 conducts adjustments for each unit of the microscope 32 necessary in the observation of the object to be inspected 343. Such adjustments are, for example, rotating the revolver to switch the objective lens 342 to be positioned in the light path of the observation light, controlling light source and switching each optical device according to the switched objective lens 342, instructing stage movement corresponding to the XY driving controller 30 and the Z driving controller 31. Then, the controller 23 arbitrarily reports status of each unit to the host system 22.

The controller 23 controls the focus detecting unit 333 to acquire the focusing status of the microscope 32 and automatically adjusting the focus of the object to be inspected by instructing the Z driving controller 31 on the stage movement according to the acquired status. In this way, the controller 23 realizes auto focusing.

Further, based on the control of the host system 22, the controller 23 switches on and off the automatic gain control functionality, sets gain, switches on and off the automatic exposing time control functionality, and sets exposing time of the camera unit 331 prior to its activation so as to control the imaging operation of the camera. Also, the controller 23 controls the measurement field of view, the measurement spots, the number of measurements, the number of integrating times, the number of channels of the multi spectral sensor, and filter settings to be utilized in spectral data acquisition conducted by the measurement unit 334.

Figure 14:
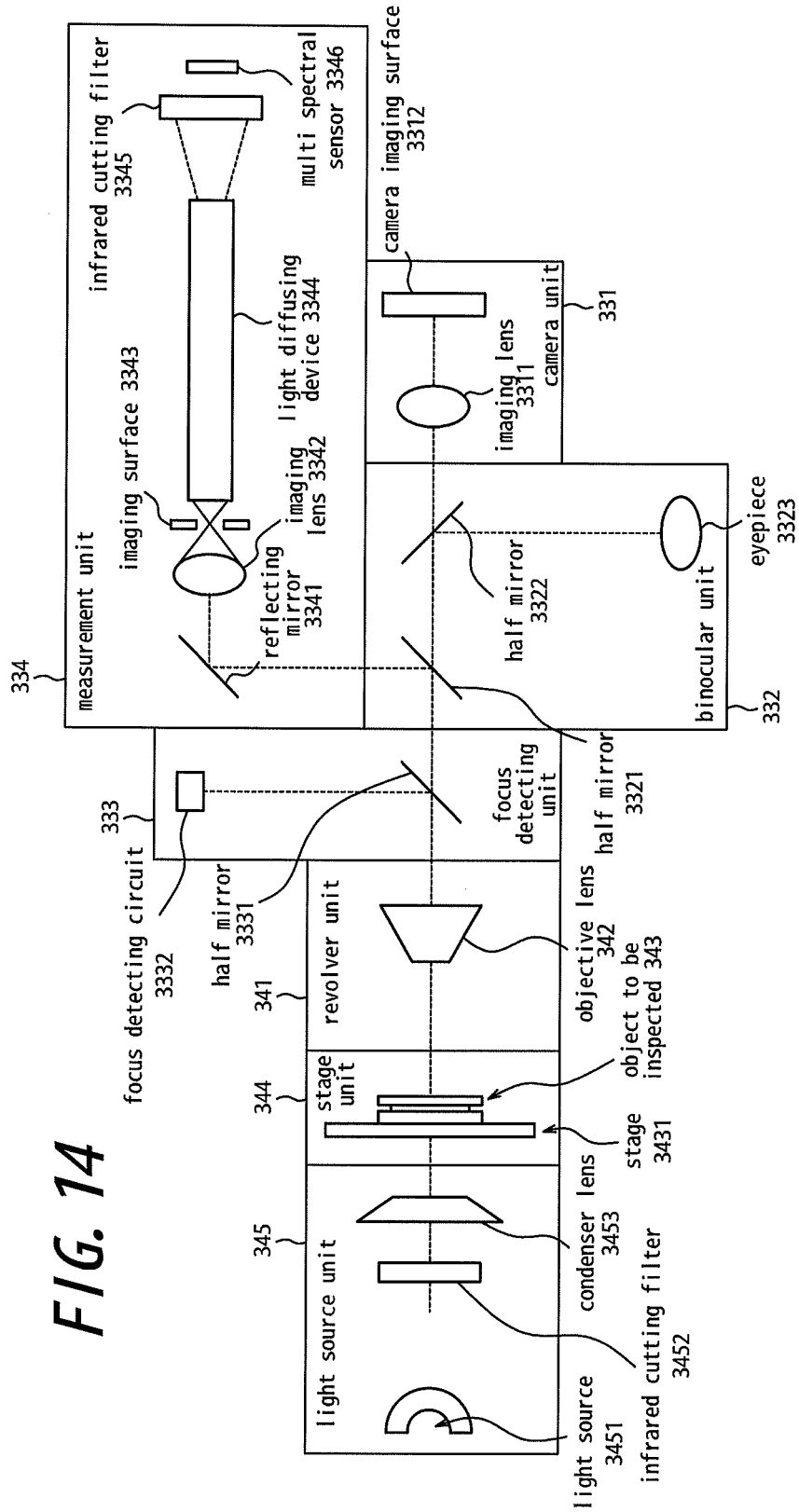
FIG. 14 is a block diagram schematically illustrating the optical configuration of the microscope system employing inspection device according to the third embodiment.

FIG. 14 is a block diagram schematically illustrating the optical configuration of the microscope system. The illumination light emitted from the light source 3451 of the light source unit 345 transmits through an infrared cutting filter 3452 and a condenser lens 3453 and illuminates the object to be inspected 343. Then, the resultant transmitted light is incident on the objective lens 342.

The light pass through the objective lens 342 is divided by a half mirror 3331 and one of the divided light is guided into a focus detecting circuit 3332 and the other divide light is guided into the binocular unit 332. The light guided into the binocular unit 332 is directed to the eyepiece 3323 by half mirrors 3321 and 3322. Accordingly, the image for inspection (image of the specimen) of the object to be inspected is observed visually by a user of the microscope.

Also, the light guided into the binocular unit 332 is directed to the camera unit 331 by the half mirrors 3321 and 3322. The light guided into the camera unit 331 is imaged at a camera imaging surface 3312 via the imaging lens 3311.

Further, the light guided into the binocular unit 332 is directed to the measurement unit 334 by the half mirror 3321. The light guided into the measurement unit 334 is imaged at an imaging surface 3343. At the imaging surface 3343, a field of view frame is provided and light within a predetermined field of view in the imaging surface 3343 will be allowed to pass. Accordingly, the field of view frame in the imaging surface 3343 can be switched (for example, the 100 μm×100 μm frame can be switched to 400 μm×400 μm frame). The light within the predetermined field of view in the imaging surface 3343 is mixed or diffused by light diffusing device 3344 (for example, an optical fiber and an integrating sphere) for normalization and emitted to the multi spectral sensor 3346. A replaceable infrared cutting filter 3345 can be arranged in front of the multi spectral sensor 3346.

The multi spectral sensor 3346 consists of a plurality of (for example, 4-20 colors of) color sensors. As to the number of color sensors to be used, that is, to the number of measurement spectral channels, the number of channels tend to be increased in the case where the object to be imaged has much information spectroscopically detected and tend to be decreased in the case where the object to be inspected does not requires high precision so as to save time spared for measurements. The information of the number of measurement spectral channels is included in the measurement information output from the condition determination unit.

In the above embodiments, the inspection device of the present invention is described referring to the exemplarily applications in the inspection of the clinical specimen. However, the inspection device can naturally be used in other type of inspections. For example, the inspection device can be utilized in inspection for a mount board. Specifically, place a board (an object to be inspected) subjected to energization for predetermined hours in the inspection device and executes image based detection of mounting defects based on a high resolution image acquired from fractional imaging. Defects can also be detected by measuring rise in heat around each determined part by temperature sensor. Examples of the resultant inspection information and measurement information are shown in Tables 10 and 11. Similar to the above embodiments, measurement information corresponding to the inspection information is determined according to the database. Thanks to this, for example, the following functionalities are realized: executing temperature measurement for prioritizing time when inspecting a thin board, varying measurement spots and conditions according to the material and thickness of the board, tightening up or loosening up measurement condition according to application of the board, varying area size for measuring temperature according to the size of parts, and varying the number of temperature measurement times and measurement interval according the density of mounted parts.

TABLE 10

| Inspection information | Contents |
| --- | --- |
| Board material | α, β, γ, . . . |
| Application of board | X, Y, Z, . . . |
| Size of mounted parts | A, B, C, . . . |
| Mounting density | High, Low, . . . |
| Board thickness | Thicker than predetermined value, Thinner than predetermined value, . . . |
| Imaging magnification | x5, x10, x20, . . . |

TABLE 11

| Measurement information | Contents |
| --- | --- |
| Number of measurement spots | One spot per one part for all parts, Three spots per one part for all parts, Once in two times of imaging, Once in ten times of imaging, . . . |
| Size of measurement area | Squares of 100 μm, 400 μm, 1 mm, . . . |
| Measurement time range | Within 500 ms from energization time, Within 2 s from energization time, . . . |
| Number of measurement times in one execution of temperature measurement | Once, five times, . . . |
| Measurement method | Temperature measurement, Determining whether the temperature is above or below a predetermined value, . . . |
| Order of measurement | Execute temperature measurement first (after completing imaging and temperature measurement of the spots requiring temperature measurement, other spots are imaged), Executing imaging sequentially in a tiling fashion and executing temperature measurement at necessary points, . . . |

In other example, the inspection device of the present invention can be utilized in evaluation of scar or color of products. Specifically, the inspection device illuminates the products moving on a manufacturing line from a fixed light source, measures spectrum of the light passed through or reflected at the products, and detects the scar on the products or difference in color. Examples of the inspection information and the measurement information are shown in Tables 12 and 13. Similar to the above embodiments, measurement information corresponding to the inspection information is determined according to the database. Thanks to this, for example, inspection can be facilitated by changing combinations of coatings and light sources and effective measurement can be realized by switching the number of measurements, wavelength, and integration times according to required levels of precision.

TABLE 12

| Inspection information | Contents |
| --- | --- |
| Used coating | α, β, γ, . . . |
| Illumination light source | X, Y, Z, . . . |

TABLE 12-continued

| Inspection information | Contents |
| --- | --- |
| Size of coated portions | A, B, C, ... |
| Imaging magnification | X1, x5, x10, ... |

TABLE 13

| Measurement information | Contents |
| --- | --- |
| Number of measurement spots | One spot per one coated portion for all coated portions, Five spots per one coated portion for all coated portions, ... |
| Size of measurement area | Squares of 100 μm, 400 μm, 1 mm, ... |
| Integrating duration in spectroscopic measurements | Once, 3 times with different integrating durations, |
| Measurement wavelength range | 500 nm-600 nm, 380 nm-780 nm, ... |
| Number of measurement times in one execution of color measurement | Once, five times, ... |

As mentioned above, it is apparent for a person skilled in the art that various changes and substitution can be made within the spirit and scope of the present invention. Thus, the present invention is not restricted to the foregoing embodiment and various changes and modifications can be made thereto.

What is claimed is:

1. An inspection device, comprising:
an imaging unit for imaging a specimen;
an imaging control unit for dividing an imaging area for the specimen into a plurality of divided imaging areas, controlling the imaging unit to image each of the plurality of divided imaging areas so as to acquire an integrated image of the imaging area;
a characteristics measurement unit for measuring spectral characteristics of the specimen;
a measurement control unit for controlling the characteristics measurement unit to selectively execute measurements synchronically with the imaging executed by the imaging control unit;
an inspection information acquisition unit for acquiring inspection information related to the specimen;
a condition determination unit for determining measurement information related to a number of measurement spots acquired by the characteristics measurement unit for the divided imaging areas and imaging information related to a number of imaging spots acquired by the imaging unit, based on the inspection information; wherein
the imaging control unit controls the imaging by the imaging unit based on the measurement information; and
the measurement control unit controls the measurement by the characteristics measurement unit based on the measurement information.

2. The inspection device according to claim 1, wherein the condition determination unit determines the imaging information related to the imaging condition of the object corresponding to the inspection information; and
the imaging control unit controls imaging by the imaging unit based on the imaging information.

3. The inspection device according to claim 1, wherein the characteristics measurement unit measures a plurality of spots for characteristics of the object.

4. The inspection device according to claim 1, further comprising:
an object moving unit for moving the object,
wherein the imaging control unit controls the object moving unit to move the object to a next divided imaging area at each time of imaging of one of the plurality of divided imaging areas.

5. The inspection device of claim 4, wherein the measurement control unit controls the characteristics measurement unit to execute additional measurements until sufficient amount of measurement data comparable to that of the number of measurement spots, after the imaging by the imaging control unit is completed, in the case where an amount of measurement data is insufficient and not comparable to that of the number of measurement spots.

6. The inspection device according to claim 4 further comprises a thumbnail acquisition unit for acquiring thumbnail by imaging the object, wherein the imaging control unit acquires location information of measurement regions within the object based on the thumbnail, controls the imaging unit to image only measurement unit existing areas, where measurement regions locate, among the divided imaging areas, controls the object moving unit to move the object so as to allow the imaging unit to image a next measurement region existing area, at each time of imaging of the measurement region existing area by imaging unit.

7. The inspection device according to claim 6 comprising the thumbnail acquisition unit for acquiring thumbnail by imaging the object and generating the inspection information from the acquired thumbnail, instead of the inspection information acquisition unit.

8. The inspection device according to the claim 7, wherein the inspection information generated by the thumbnail acquisition unit includes color information of the thumbnail.

9. The inspection device according to the claim 8, wherein the measurement information includes information representing determining the randomly selected spots among imaging spots as measurement spots or determining the evenly and discretely selected spots from the imaging spots as the measurement spots.

10. The inspection device according to the claim 1, wherein the object is a stained specimen.

11. The inspection device according to claim 10, wherein the characteristics measurement unit has a multispectral sensor.

12. The inspection device according to claim 1, wherein a measurement field of view of the measurement unit corresponds to a part of the imaging field of view of the imaging unit.

13. The inspection device according to claim 1, wherein the imaging information further includes imaging magnification.

14. The inspection device according to claim 1, wherein the inspection information includes any of a facility where the object was prepared, a staining method applied for the object, an organ type, a thickness, and image information.

15. The inspection device according to claim 1, wherein the measurement information includes any of channels used by a multispectral sensor provided in the characteristics measurement unit, integrating duration of the multispectral sensor, sensitivity of the multispectral sensor, integrating times.

* * * * *